(12) United States Patent
Temple

(10) Patent No.: US 6,318,150 B1
(45) Date of Patent: Nov. 20, 2001

(54) APPARATUS FOR SAMPLING GAS IN A COMBUSTION APPLIANCE

(75) Inventor: Keith A. Temple, Addison, TX (US)

(73) Assignee: Lennox Manufacturing Inc., Richardson, TX (US)

( * ) Notice: Subject to any disclaimer, the term of this patent is extended or adjusted under 35 U.S.C. 154(b) by 0 days.

(21) Appl. No.: 09/183,894

(22) Filed: Oct. 30, 1998

(51) Int. Cl.$^7$ ........................................................ G01N 1/22
(52) U.S. Cl. .................... 73/23.31; 73/31.01; 73/863.11; 73/863.61; 432/32
(58) Field of Search ............................. 73/863.11, 23.11, 73/863.61, 31.02, 863.12, 31.01; 432/32

(56) References Cited

U.S. PATENT DOCUMENTS

| 1,658,391 | * | 2/1928 | Potter ................................. 73/23.31 |
| 3,960,500 | * | 6/1976 | Ross et al. ........................ 73/23.31 X |
| 3,965,749 | * | 6/1976 | Hadden et al. ................ 73/863.61 X |
| 4,115,229 | * | 9/1978 | Capone ........................... 73/23.31 X |
| 4,485,684 | * | 12/1984 | Weber et al. .................. 73/23.31 X |
| 4,561,288 |   | 12/1985 | Moenkhaus .................... 73/863.61 X |
| 5,239,980 |   | 8/1993 | Hilt et al. ........................ 126/116 A |
| 5,456,124 | * | 10/1995 | Colvin ............................... 73/863.11 |
| 5,477,913 |   | 12/1995 | Polk et al. ............................. 165/12 |
| 5,576,739 |   | 11/1996 | Murphy .......................... 340/825.06 |
| 5,600,057 |   | 2/1997 | Hansche et al. ..................... 73/40.7 |

FOREIGN PATENT DOCUMENTS

| 2136912 | * | 2/1973 | (DE) ................................. 73/863.11 |
| 390 941 A1 | * | 10/1990 | (EP) .................................. 73/23.31 |
| 2-187638 | * | 7/1990 | (JP) .................................. 73/23.31 |
| 3-246456 | * | 11/1991 | (JP) .................................. 73/23.31 |

OTHER PUBLICATIONS

Gas Research Institute—Improved Heat Exchanger Service Test Brochure, Jun. 1985, 3 pages.
Patent Abstracts of Japan (62151736 A) Jul. 1987.
Patent Abstracts of Japan (5506672.9A) May 1980.
D.L. Hammond, "A Proportionate Gas Sampler", ISA Journal, May 1963, pp. 73–76 in 73/863.61.*

* cited by examiner

Primary Examiner—Thomas P. Noland
(74) Attorney, Agent, or Firm—W. Kirk McCord

(57) ABSTRACT

Apparatus is provided for sampling gas in operative association with a combustion appliance, such as a furnace. The combustion appliance includes a first conduit through which combustion air is supplied to the appliance and a second conduit through which gas heated by the appliance is discharged from the appliance. The sampling apparatus includes a third conduit communicating between the first and second conduits and a gas sensor operable to sense a selected gas in the heated gas present in the third conduit. Operation of the appliance creates a pressure difference between the first and second conduits to draw a sample of heated gas from the second conduit into the third conduit, so that no mechanical device, such as a pump, is needed to transport the sample of heated gas to the gas sensor. A temperature sensor is provided for sensing temperature of the gas in the third conduit to verify gas flow in the third conduit. If the temperature sensor does not sense at least a predetermined increase in temperature during a predetermined period of appliance operation, it indicates insufficient gas flow in the third conduit for sampling purposes. The gas sampling apparatus may be used to detect products of combustion leakage in combustion appliances as well as to measure the concentration of a selected gas, such as carbon monoxide.

10 Claims, 10 Drawing Sheets

APPARATUS FOR SAMPLING GAS IN A COMBUSTION APPLIANCE

FIELD OF INVENTION

This invention relates generally to combustion appliances and in particular to improved apparatus for sampling gas in a combustion appliance.

BACKGROUND ART

Prior art apparatus for sampling gas in operative association with a combustion appliance, such as a furnace, boiler or water heater, have typically involved the use of a mechanical device, such as a pump, or a specially configured sampling conduit to provide a pressure difference needed to sustain a flow of gas to be sampled to a gas sensor, which is operable to measure concentration of a selected gas. A device is also needed to verify that there is sufficient gas flow to the sensor for sampling purposes. Such prior art apparatus usually focus on quantitative measurement of the gas flow and may have one or more of the following disadvantages: (1) difficulty in detecting relatively low flow rates; (2) insensistivity to flow direction; (3) flow restrictions; and (4) relatively high cost.

One application of gas sampling is to detect the presence of potentially dangerous gases, such as carbon monoxide, in the products of combustion of a furnace or in the heated air supplied by the furnace to an indoor space. Products of the combustion process are typically exhausted from the furnace through a flue after passing through a heat exchanger. An air mover, such as a blower, moves the supply air across the heat exchanger, whereby heat is transferred from the products of combustion to the air. The heated air is then supplied to an indoor space. One type of fuel used in furnaces, such as furnaces used to heat residences, is natural gas. Products of combustion of natural gas usually include water vapor, carbon dioxide and sulfur dioxide, and in the event of incomplete combustion of the natural gas, carbon monoxide. Although carbon monoxide is known to be hazardous to human health, it is usually not produced in large enough concentrations to present a danger to human beings, if the furnace is operating properly. Further, whatever carbon monoxide is produced should be confined to the inside of the heat exchanger and flue, so that under normal circumstances carbon monoxide should not be present in the supply air. However, if there is a leak in the heat exchanger, products of combustion, which may include carbon monoxide, can escape into the supply air and enter the indoor space.

Prior art techniques for preventing carbon monoxide from reaching dangerous levels in an indoor space have generally involved installation of a carbon monoxide detector either in the space or in a supply air plenum or duct downstream of the heat exchanger. A carbon monoxide detector can also be used to detect carbon monoxide in the products of combustion exhausted through the flue. The detector may generate an alarm in response to the concentration of carbon monoxide being in excess of a predetermined level, which may result in the furnace being automatically deactivated. However, carbon monoxide detectors are often unreliable and susceptible to false alarms. Also, such detectors may not be sensitive enough to accurately measure relatively low concentrations of carbon monoxide because of diffusion of the carbon monoxide gas in the supply air stream and indoor space.

In lieu of using detectors to directly measure carbon monoxide concentrations, the presence, or potential presence, of carbon monoxide in the supply air stream may be inferred if a products of combustion leak is detected in the furnace. Various procedures are known in the art for detecting products of combustion leakage from furnace components, such as heat exchangers, combustion chambers and the like. One such procedure involves introducing a non-combustible tracer gas, such as a combination of methane and nitrogen, into the heat exchanger and using a gas detector to detect the presence of any tracer gas in the supply air stream. The presence of tracer gas in the supply air stream indicates a leak in the heat exchanger through which products of combustion can escape into the supply air stream. Another procedure involves introducing a fine mist of liquid fire retardant material into the return air stream upstream of the heat exchanger and determining whether there is a change in the color of the flame in the furnace combustion chamber. A change in color from blue to orange indicates a leak in the combustion chamber wall. Other techniques involve pressurizing the heat exchanger to detect leaks. The primary disadvantages of these leak detection procedures are that they require introduction of an external gas or other fluid and the presence of a service person and special equipment.

There is, therefore, a need for an improved apparatus for sampling gas in a combustion appliance. There is also a need for an improved apparatus for detecting products of combustion leakage in a combustion appliance.

SUMMARY OF THE INVENTION

In accordance with the present invention, apparatus is provided for sampling gas in operative association with a combustion appliance, such as a furnace, boiler or water heater. The combustion appliance includes a first conduit through which combustion air is supplied to the appliance and a second conduit through which gas is discharged from the appliance after being heated. The sampling apparatus includes a third conduit communicating between the first and second conduits and a gas sensor operable to determine whether a selected gas is present in the heated gas. Operation of the appliance creates a pressure difference between the first and second conduits to draw a sample of heated gas from the second conduit into the third conduit. The gas sensor senses whether the selected gas is present in the sample of heated gas in the third conduit. In accordance with a feature of the invention, a temperature sensor is provided for sensing temperature of the heated gas in the third conduit to verify gas flow in the third conduit. If the temperature sensor does not sense at least a predetermined increase in temperature during a predetermined period of appliance operation, it indicates insufficient flow of the heated gas in the third conduit for sampling purposes.

In accordance with one application of the present invention, the gas sampling apparatus is operatively associated with a combustion appliance, such as a furnace, boiler or water heater to detect products of combustion leakage in the appliance. A gas sensor is provided to sense a selected gas known to be present in the products of combustion, such as carbon dioxide, in a gas sample taken externally to products of combustion carrying components of the appliance. A controller is provided to control the gas sensor to measure the concentration of the selected gas during a predetermined period of appliance operation and to determine whether there is an increase in the concentration during the predetermined period. An increase in concentration may be attributable to a leak in a products of combustion carrying component of the appliance. A temperature sensor is provided for measuring the temperature of the gas sample during the predetermined period. If the temperature sensor does not detect at least a predetermined increase during the predetermined period, it indicates insufficient flow of the sample to the gas sensor.

In accordance with another application of the present invention, the gas sampling apparatus is used to sense the presence of a selected gas, such as carbon monoxide, in the products of combustion of a combustion appliance, such as a furnace, boiler or water heater. In this application, a sampling conduit communicates between a combustion air intake conduit through which combustion air is supplied to the appliance and a flue through which products of combustion are exhausted from the appliance. Operation of the appliance draws a sample of the products of combustion from the flue into the sampling conduit. A gas sensor is operable to sense the selected gas in the products of combustion sample and to measure the concentration thereof during a predetermined period of appliance operation. A temperature sensor is provided for measuring the temperature of the sample of products of combustion in the sampling conduit during the predetermined period. If the temperature sensor does not detect at least a predetermined increase during the predetermined period, it indicates insufficient flow of products of combustion through the sampling conduit to the gas sensor.

BEST MODE FOR CARRYING OUT THE INVENTION

In the description which follows, like parts are marked throughout the specification and drawings with the same respective reference numbers. The drawings are not necessarily to scale and in some instances proportions may have been exaggerated in order to more clearly depict certain features of the invention.

Figure 1:
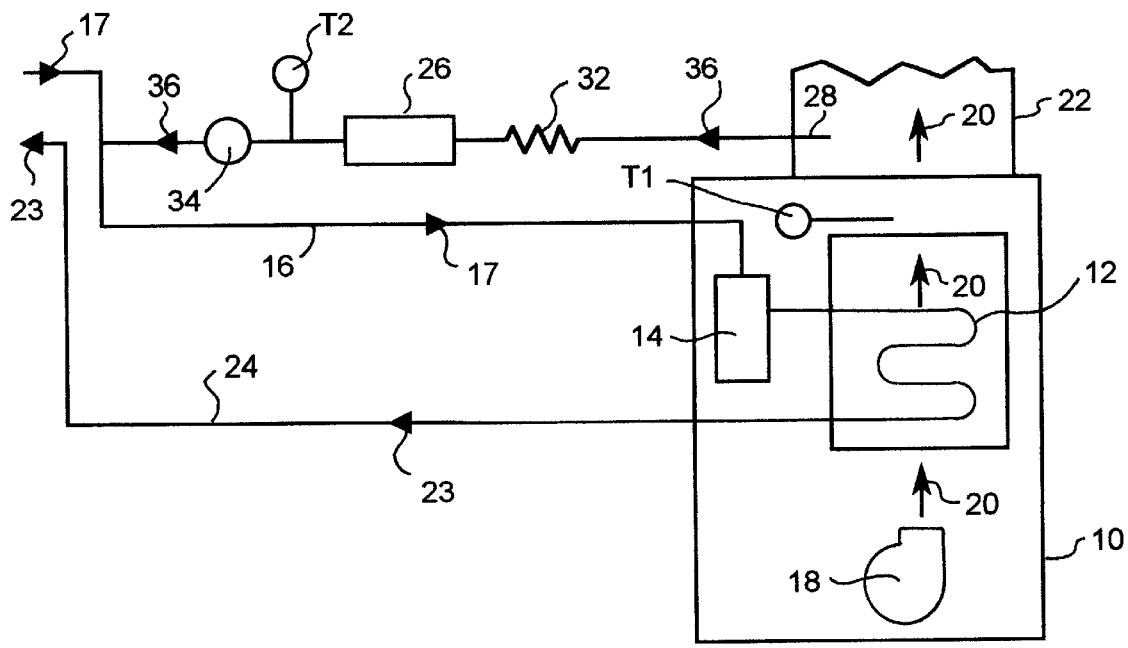
FIG. 1 is a schematic diagram of a furnace and apparatus for detecting a leak in the furnace heat exchanger, according to the present invention.

Referring to FIG. 1, a fuel-burning furnace 10 includes an igniter (not shown) for igniting a combustible fuel-air mixture at furnace start-up and a burner assembly (not shown) for burning the fuel-air mixture when the furnace is in operation. Furnace 10 also includes a heat exchanger 12 for receiving products of the combustion process, a combustion air blower 14 for supplying combustion air to furnace 10 through an air intake conduit 16 in the direction of arrows 17 and a supply air blower 18 for blowing ambient air across heat exchanger 12 in the direction of arrows 20, whereby the ambient air is heated by heat exchanger 12 and supplied to an indoor space via a supply air duct 22. In addition to supplying combustion air for furnace 10, combustion air blower 14 also exhausts products of combustion from furnace 10 in the direction of arrows 23 through a flue 24 at the outlet of heat exchanger 12.

In accordance with the present invention, apparatus is provided for detecting the presence of a leak in heat exchanger 12. The apparatus includes a gas sensor 26 and a sampling tube 28, which is in fluid communication between supply air duct 22 and air intake conduit 16 for conducting a sample of supply air 20 to gas sensor 26. Gas sensor 26 is preferably a carbon dioxide sensor of the type which uses infrared technology to measure the concentration of carbon dioxide in the air flowing through tube 28. For example, sensor 26 may be a gas sensor of the type sold by Engelhard Corporation, of Goleta, Calif., under Model No. Ventostat 8000 or by Texas Instruments Incorporated, of Versailles, Ky., under Model No. 4GS.

A first temperature sensor T1, preferably a thermistor, is located in supply air stream 20, proximate to heat exchanger 12 and slightly downstream thereof, to measure a temperature which corresponds to the temperature of heat exchanger 12. A second temperature sensor T2, also preferably a thermistor, is positioned to measure the temperature of the sample of supply air within tube 28. Although not required, an auxiliary heater 32 may be provided to heat the sample of supply air flowing through tube 28 before the air reaches gas sensor 26 and temperature sensor T2. Heater 32 is preferably an electric heater of the type sold by Chicago Miniature Lamp, of Hackensack, N.J., under Model No. 7152. Although not required, an air pump 34 may be provided to increase the flow of air through tube 28. Pump 34 is preferably an air pump of the type sold by Apollo, of Ontario, Calif., under Model No. 3000 or by KNF Neuberger, of Trenton, N.J., under Model No. NMPO8.

When blower 14 is in operation, there is a negative pressure in conduit 16 on the suction side of blower 14. Because sampling tube 28 is in fluid communication with conduit 16, the negative pressure in conduit 16 draws supply air 20 into sampling tube 28 in the direction of arrows 36. Pump 34 may be used to enhance the flow of air through tube 28. Temperature sensor T2 is used to determine whether there is sufficient flow of supply air through tube 28 for sampling purposes. This is accomplished by measuring the temperature of the air within tube 28 as furnace 10 warms up at the beginning of a heating cycle. As furnace 10 warms up, supply air 20 is heated by heat exchanger 12, so that temperature sensor T2 should detect an increase in temperature of the supply air in tube 28. This increase in temperature is an indication of flow within sampling tube 28. Auxiliary heater 32 may be used to add heat to the air before it reaches gas sensor 26 and temperature sensor T2, which facilitates detection of a temperature increase by temperature sensor T2.

Gas sensor 26 is used to measure the concentration of carbon dioxide in supply air 20 downstream of heat exchanger 12. A baseline or ambient concentration is measured when heat exchanger 12 is "cold", prior to the onset of furnace combustion. However, even though furnace 10 is not in operation, blower 14 is preferably operated to draw a sample of supply air 20 into tube 28. Alternatively, in lieu of operating blower 14, pump 34 can be used to draw supply air 20 into tube 28. The concentration of carbon dioxide in supply air 20 measured prior to the onset of furnace combustion is attributable to occupants of the indoor space or other sources besides furnace 10.

When furnace 10 commences operation, heat exchanger 12 begins to warm up. Sensor 26 continues to measure the carbon dioxide concentration in supply air 20 during a predetermined sampling period. If the carbon dioxide level increases by more than a predetermined amount during the sampling period compared to the baseline or ambient air concentration, one can infer that the increase is attributable to products of combustion leaking from heat exchanger 12 into supply air stream 20.

Figure 2:
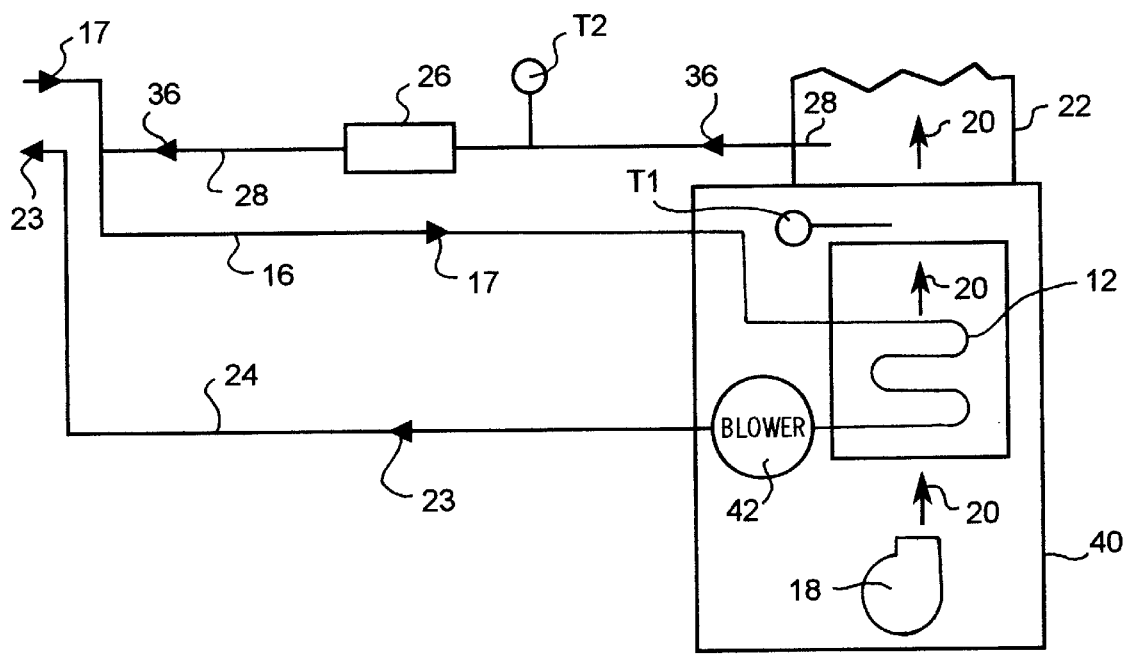
FIG. 2 is a schematic diagram of an alternate embodiment of the furnace and leak detection apparatus.

Referring to FIG. 2, the leak detection apparatus according to the present invention is depicted in operative association with a furnace 40. Furnace 40 is the same as furnace 10, described hereinabove with reference to FIG. 1, except that combustion air blower 14 is replaced by an induced draft blower 42. Blower 42 draws combustion air through conduit 16 into furnace 10 and exhausts products of combustion through flue 24 by induction. Also, the leak detection apparatus associated with furnace 40 is depicted without the optional auxiliary heater 32 and pump 34 and temperature sensor T2 is on the upstream side of carbon dioxide sensor 26 instead of on the downstream side thereof, as in FIG. 1. Otherwise, the operation of the leak detection apparatus is the same as described hereinabove with reference to FIG. 1.

In another embodiment (not shown), the leak detection apparatus according to the present invention may be used in operative association with a furnace of the pulse combustion type. In this type of furnace, a purge blower is used in lieu of combustion air blower 14 or induced draft blower 42 to provide combustion air to the furnace at the beginning of furnace operation. After the onset of combustion, the combustion process itself draws combustion air into the furnace and exhausts products of combustion therefrom.

Figure 3:
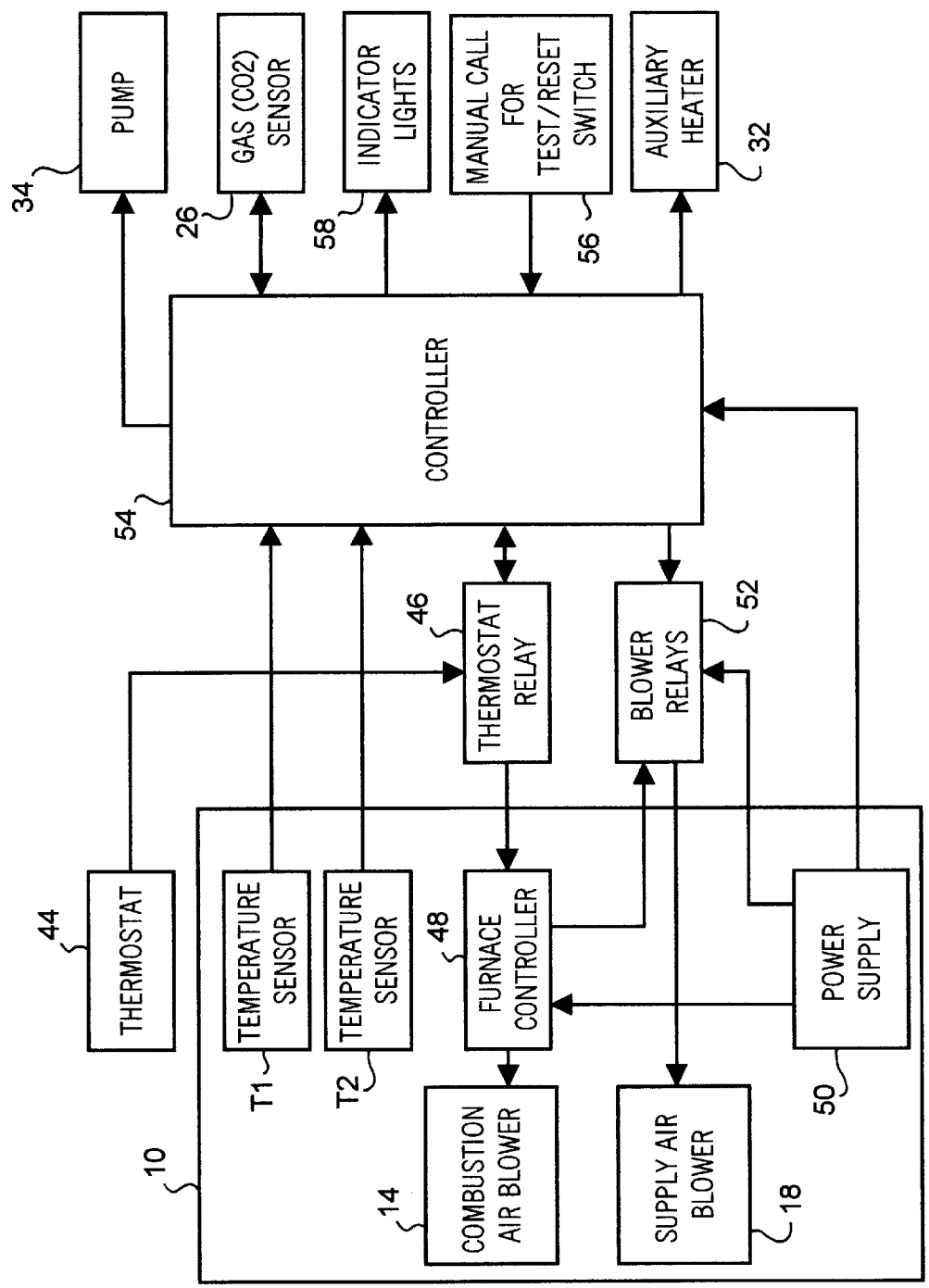
FIG. 3 is a block diagram of the major electrical components of the leak detection apparatus.

Referring to FIGS. 3–12, the operation of the leak detection apparatus, according to the present invention, is described in greater detail. Referring specifically to FIG. 3, an indoor thermostat 44 is used to activate and deactivate furnace 10. When there is a demand for heat in the indoor space to which heated air is supplied by furnace 10, thermostat 44 sends a signal via a thermostat relay 46 to a furnace controller 48, which in turn activates furnace 10. Electrical power is supplied to furnace controller 48 by a power supply 50. When the furnace is activated, furnace controller 48 activates, among other components, combustion air blower 14 and supply air blower 18 via blower relays 52. Typically, three relays are associated with supply air blower 18, one for ventilation, one for cooling and one for heating, as one skilled in the art will readily appreciate.

A controller 54, preferably a microcontroller of the PIC 16CXX series, manufactured and sold by Microchip Technology, of Chandler, Ariz., is programmed to control the leak detection operation, as will be described in greater detail with reference to FIGS. 4–12. Controller 54 is also powered by power supply 50 and also receives the demand for heat signal from thermostat 44 via relay 46. Further, controller 54 is operable to interrupt the demand for heat signal from thermostat 44. A signal interrupting the demand for heat signal is sent by controller 54 to furnace controller 48 via thermostat relay 46.

Controller 54 also controls supply air blower 18 via blower relays 52. As also shown in FIG. 3, controller 54 receives input signals from temperature sensors T1 and T2, from a manual call for test/reset switch 56 and from gas sensor 26. Controller 54 also controls the operation of auxiliary heater 32, sampling pump 34 and plural indicator lights 58, which are used to indicate an alarm or fault condition, as will be described in greater detail hereinafter.

Figure 4:
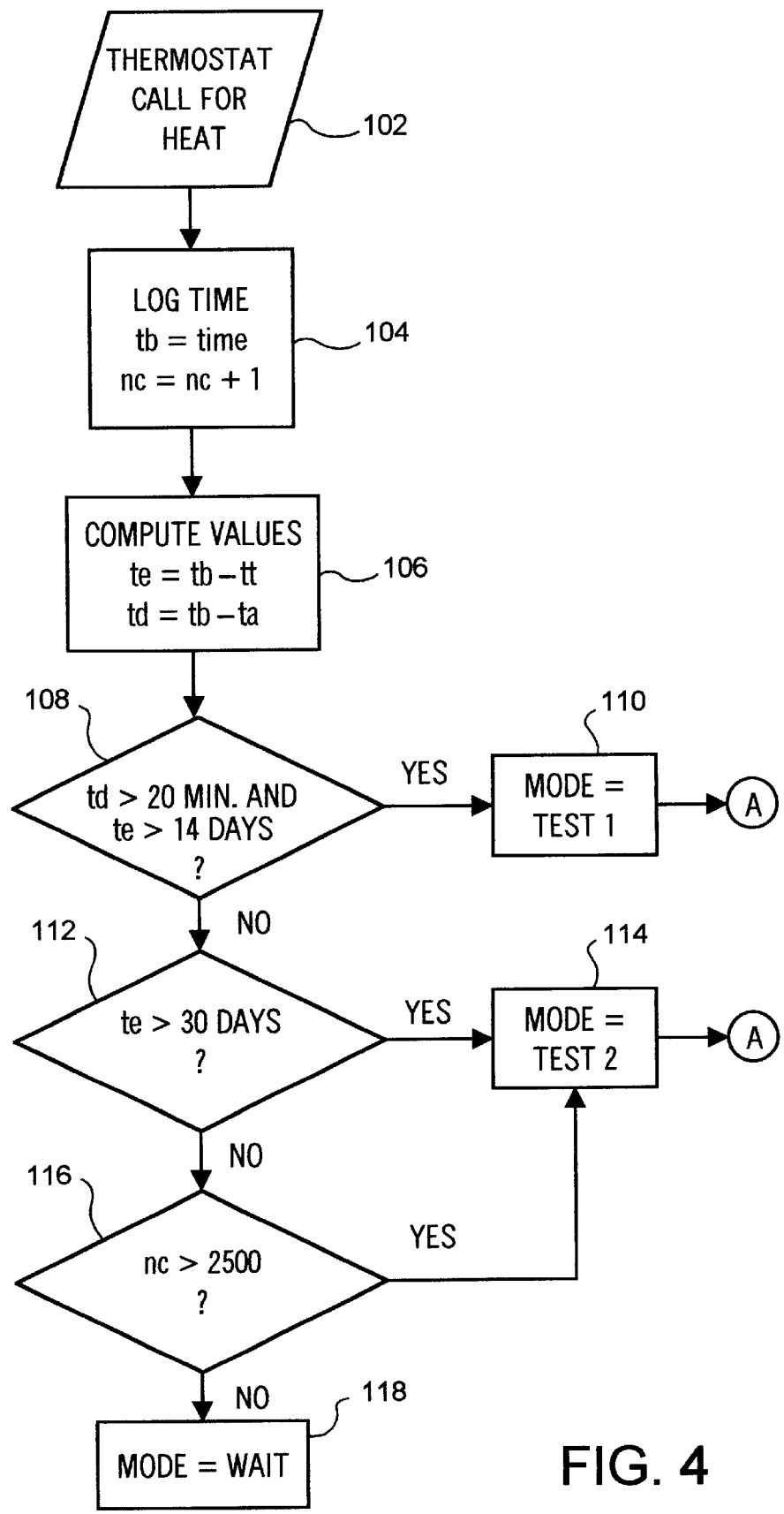
FIGS. 4–12 are flow diagrams showing the control logic for the leak detection apparatus.
Figure 5:
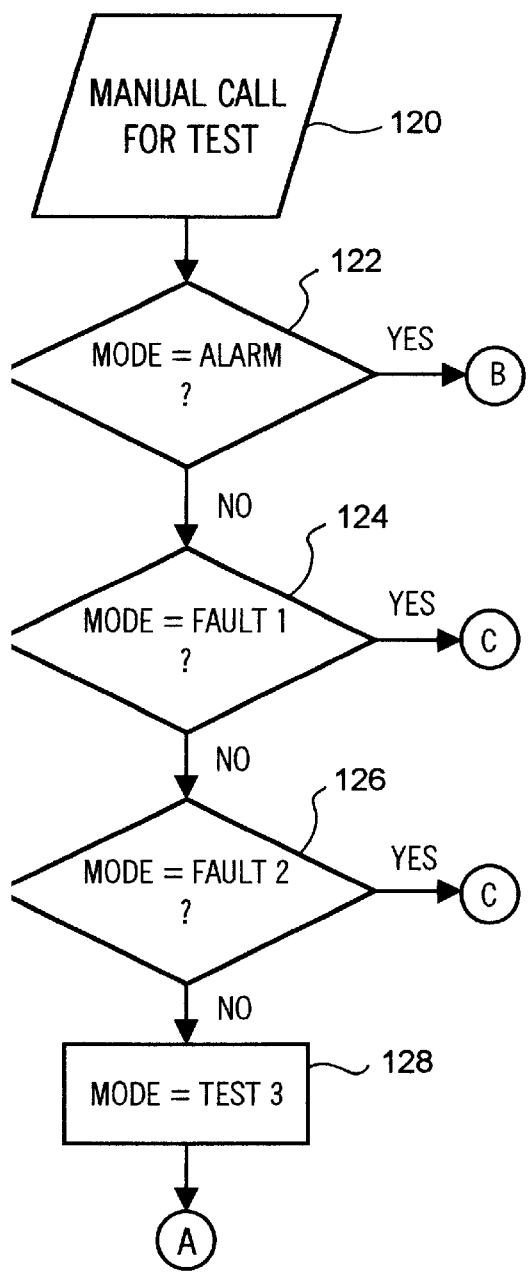

Referring to FIGS. 3–6, the leak detection method according to the present invention is typically initiated in response to a call for heat from thermostat 44 (FIG. 4) or a manual call for test (FIG. 5). As shown in FIG. 4, in response to a thermostat call for heat (step 102), controller 54 logs the time of the call for heat (tb) and increments the cycle count (nc) by one (nc=nc+1), pursuant to step 104. The cycle count (nc) represents the number of heating cycles since the last leak detection test was performed. Pursuant to step 106, the elapsed time since the last leak detection test (te) is computed by subtracting the time at which the last test occurred (tt) from the time of the present call for heat (tb). The time between the last two calls for heat (td) is also computed by subtracting the time of the previous call for heat (ta) from the time of the present call for heat (tb). Alternatively, td can represent the time that the furnace has been off, which is the time between the end of the last heating cycle and the present call for heat.

After the aforementioned values have been computed, controller 54 determines whether td has exceeded twenty minutes and whether the elapsed time since the last leak detection test (te) has exceeded fourteen days, pursuant to step 108. If td is greater than twenty minutes and te is greater than fourteen days, a leak detection test will be performed in a TEST 1 MODE, pursuant to step 110, beginning at A in FIG. 9, which will be described in greater detail hereinafter. If td is not greater than twenty minutes or if te is not greater than fourteen days, controller 54 determines whether te is greater than thirty days, pursuant to step 112. If te is greater than thirty days, a leak detection test will be performed in a TEST 2 MODE, pursuant to step 114, beginning at A in FIG. 9. The major difference between the TEST 1 MODE and the TEST 2 MODE is that the TEST 2 MODE is executed when the time between the last two calls for heat (td) has not been greater than twenty minutes. As such, the TEST 2 MODE may be executed when the furnace heat exchanger is still relatively warm.

If, pursuant to step 112, it is determined that te is not greater than thirty days, controller 54 next determines whether the number of heating cycles since the last leak detection test (nc) is greater than 2500, pursuant to step 116. If so, a leak detection test will be performed in the TEST 2 MODE. If not, controller 54 goes into a WAIT MODE in accordance with step 118. In the WAIT MODE, controller 54 waits until the next call for heat from thermostat 44 or a manual call for test, whichever occurs first.

FIG. 5 shows the routine in response to a manual call for test, pursuant to step 120. The manual call for test is initiated when the manual call for test/reset switch 56 (FIG. 3) is operated. In response to a manual call for test, controller 54 will execute a routine depending upon what mode the controller is in when the manual call for test is received. If the current mode is an ALARM MODE (step 122), controller 54 will execute an alarm routine, beginning at B in FIG. 7, which will be described in greater detail hereinafter. If the current mode is a FAULT 1 MODE (step 124), controller 54 will execute a fault routine, beginning at C in FIG. 8, which will be described in greater detail hereinafter. If the current mode is a FAULT 2 MODE (step 126), the fault routine will be executed, beginning at C in FIG. 8. If, however, the current mode is none of the aforementioned alarm or fault modes, a leak detection test will be performed in a TEST 3 MODE (step 128), beginning at A in FIG. 9.

Figure 6:
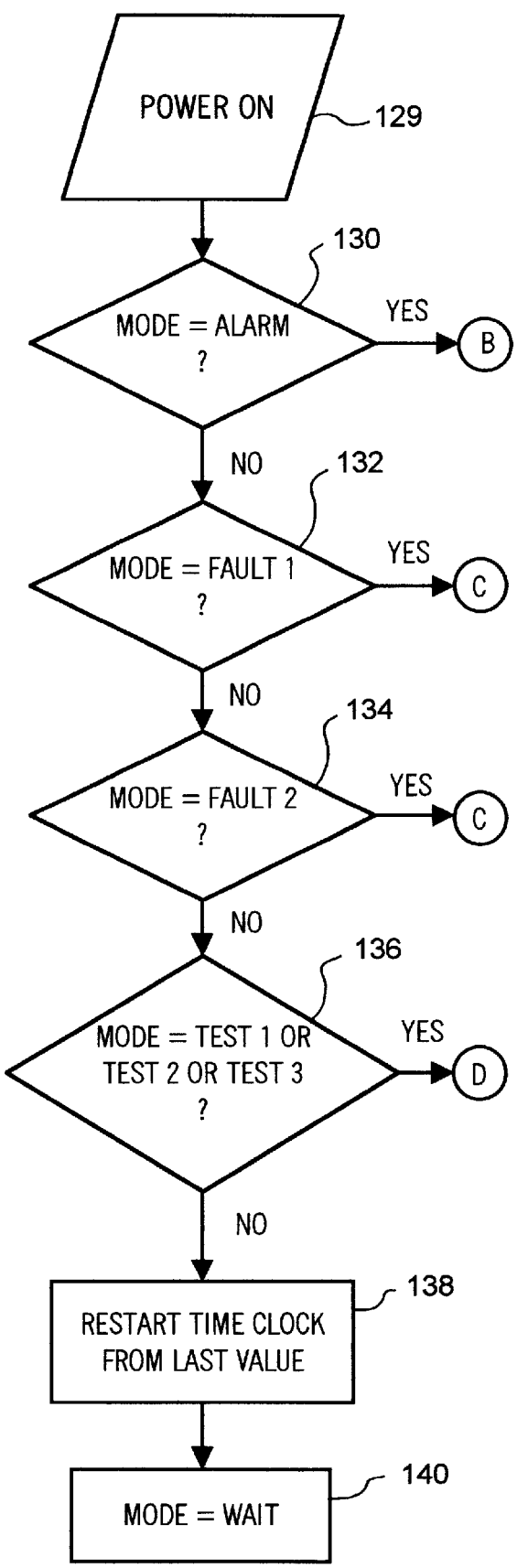
Figure 7:
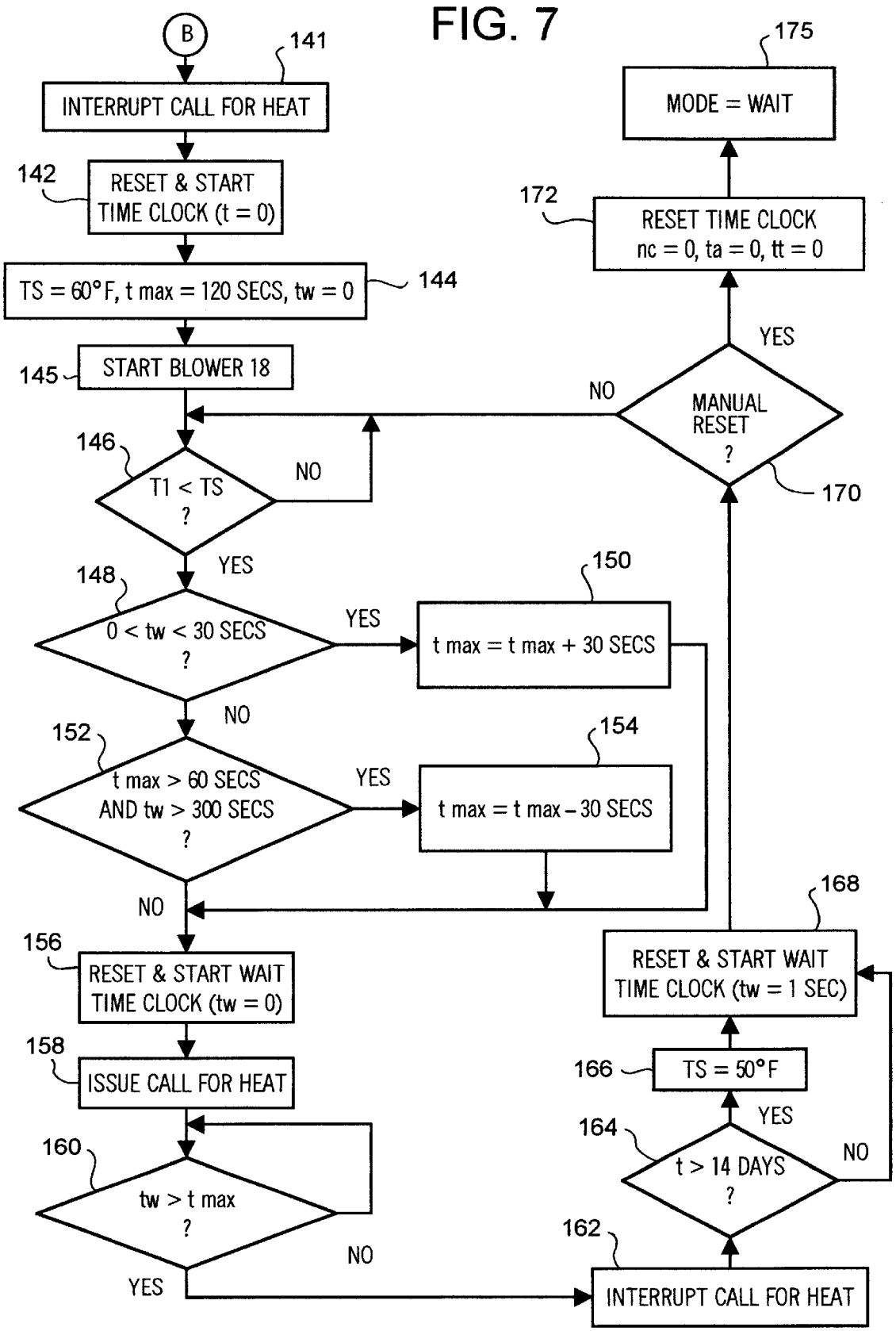
Figure 8:
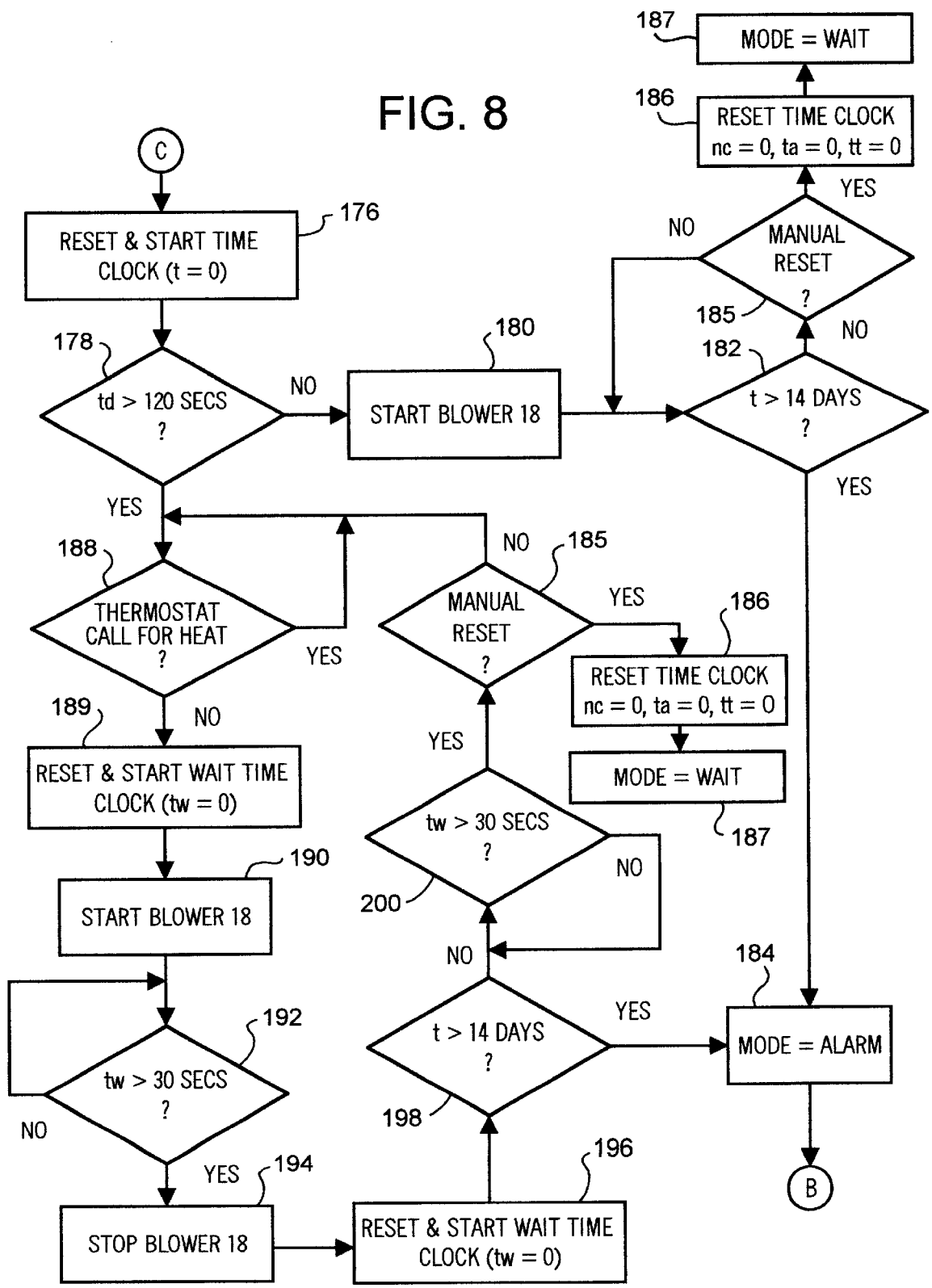
Figure 9:
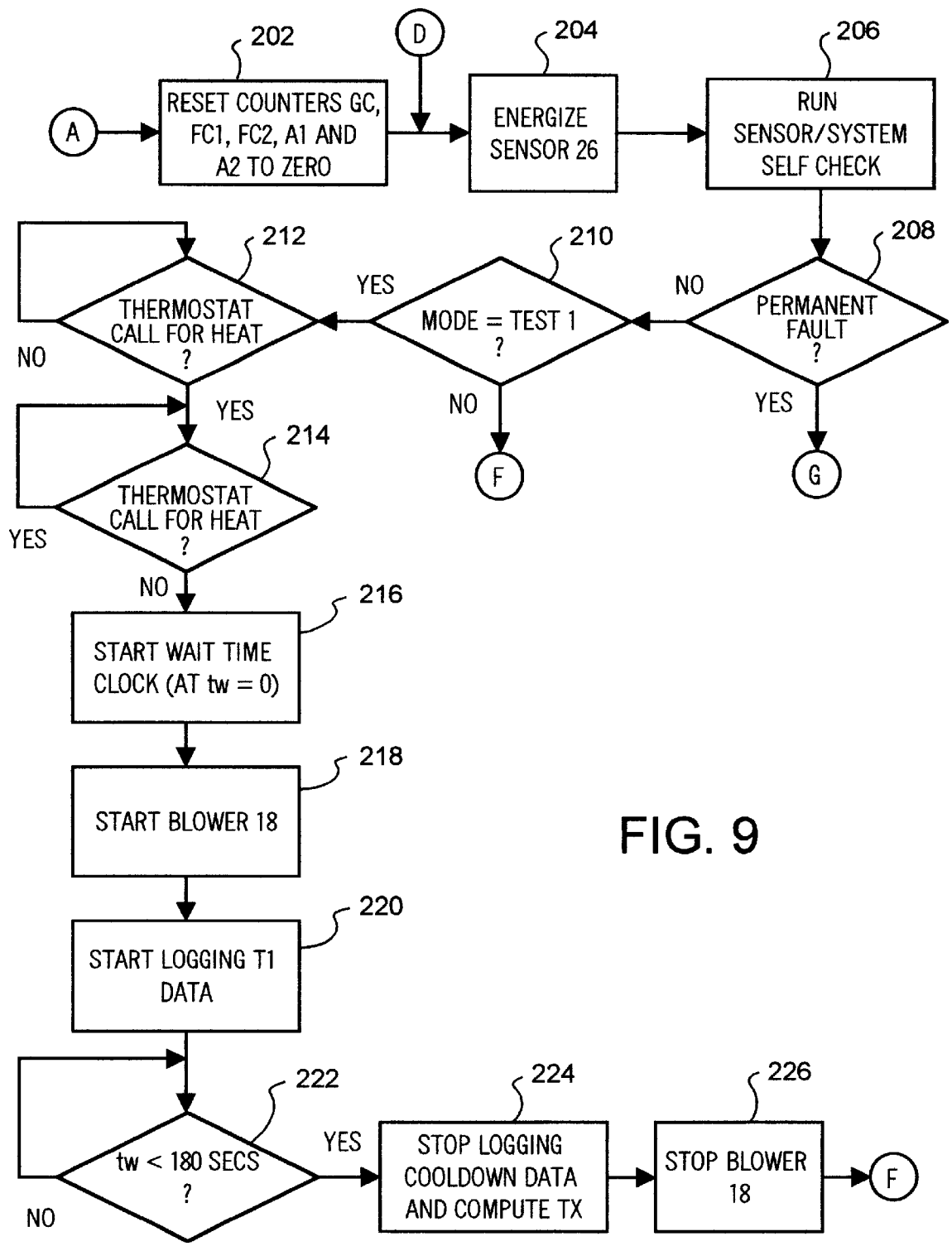

As shown in FIG. 6, in response to initial application of power (step 129) to controller 54, controller 54 will execute the alarm routine, beginning at B in FIG. 7, if the ALARM MODE is indicated, pursuant to step 130, and will execute the fault routine, beginning at C in FIG. 8, if either the FAULT 1 MODE is indicated, pursuant to step 132, or the FAULT 2 MODE is indicated, pursuant to step 134. If none of the aforementioned alarm or fault modes is indicated, controller 54 will determine whether the current mode is the TEST 1 MODE, the TEST 2 MODE or the TEST 3 MODE, pursuant to step 136. If any of the three test modes is indicated, the corresponding leak detection test is performed, beginning at D in FIG. 9. If, however, none of the leak detection test modes is indicated, the time clock is restarted, pursuant to step 138, and controller 54 goes into the WAIT MODE (step 140) until the next call for heat signal is received from thermostat 44.

Referring now to FIGS. 3 and 7, the routine which is executed in response to the ALARM MODE is depicted. As will be described in greater detail hereinafter, the ALARM MODE is indicated in response to gas sensor 26 measuring a substantial increase in carbon dioxide concentration during the predetermined sampling period. A substantial increase in carbon dioxide concentration is indicative of a potential leak in the furnace heat exchanger. Pursuant to step 141, a call for heat from thermostat 44 is interrupted and pursuant to step 142, the controller time clock is reset and restarted (t=0). The temperature setpoint (TS) for temperature sensor T1 (which is proximate to the furnace heat exchanger and slightly downstream thereof) is set at 60° F., the time that the furnace is allowed to operate (tmax) is set initially at 120 seconds and controller 54 begins to measure the wait time (tw), which corresponds to the time it takes for the heat exchanger temperature to drop down to 60° F. after the furnace is turned off, pursuant to step 144. Blower 18 (FIG. 3) is started, pursuant to step 145.

When the ALARM MODE is indicated, controller 54 will control furnace operation so as to override the call for heat signal from thermostat 44. The furnace will be operated for a predetermined time (tmax) and then will be turned off and kept off until the temperature measured by sensor T1 is less than setpoint TS, pursuant to step 146. After the heat exchanger temperature (T1) has fallen below TS, controller 54 determines whether it took fewer than thirty seconds for the heat exchanger temperature to fall below setpoint TS, pursuant to step 148. If fewer than thirty seconds were required, tmax (the maximum time the furnace is operated in the ALARM MODE) is increased by thirty seconds, pursuant to step 150, so that the furnace will be operated for thirty seconds longer the next time it is operated. However, if more than 300 seconds are required for the heat exchanger to cool down below setpoint TS and tmax is greater than sixty seconds (step 152), tmax will be decreased by thirty seconds, pursuant to step 154, so that the furnace will be operated for thirty seconds less the next time it is operated. If both conditions of step 152 are not satisfied, tmax remains unchanged and the wait time clock is reset (tw=0) and restarted, pursuant to step 156, and controller 54 will allow the call for heat signal from thermostat 44 to activate the furnace, pursuant to step 158.

The furnace remains activated for a time equal to tmax. When the wait time (tw) exceeds tmax (step 160), the call for heat is interrupted, even if the thermostat demand has not been satisfied, pursuant to step 162. If the elapsed time since the time clock was started in step 142 has exceeded fourteen days (step 164), the heat exchanger setpoint temperature (TS) is lowered to 50° F., pursuant to step 166. Irrespective of whether the time clock count exceeds fourteen days, the wait time clock is reset to one second (tw=1) and restarted, pursuant to step 168.

The ALARM MODE routine is iteratively executed until manual call for test/reset switch 56 (FIG. 3) is operated to indicate a system reset, pursuant to step 170. Upon receipt of the manual reset signal, the time clock (t), the time of the previous call for heat (ta) and the time of the last leak detection test (tt) are reset to zero. The cycle counter (nc) is also reset to zero, pursuant to step 172. Controller 54 then goes into the WAIT MODE, pursuant to step 175. One skilled in the art will recognize that in the ALARM MODE the furnace is allowed to operate for a relatively short time (tmax), such that the demand for heat in an indoor space will probably not be satisfied. Therefore, an occupant of the indoor space will be alerted to a potential problem indicated by operation of the furnace in the ALARM MODE.

Referring to FIGS. 3 and 8, the routine is depicted which is executed in response to either the FAULT 1 MODE or the FAULT 2 MODE. The FAULT 1 MODE indicates a problem with a component in the leak detection apparatus, while the FAULT 2 MODE indicates a problem in a furnace component external to the leak detection apparatus. Pursuant to step 176, the time clock is reset (t=0) and restarted. If the time between the last two calls for heat (td) is not greater than 120 seconds (step 178), blower 18 is started, pursuant to step 180, and if the elapsed time since the time clock was started in step 176 exceeds fourteen days (step 182), the ALARM MODE is indicated (step 184) and controller 54 will execute the alarm routine, beginning at B in FIG. 7. However, if the elapsed time is not greater than fourteen days (step 182) and there is a manual reset (step 185), the time clock (t), the time of the previous call for heat (ta), the time of the last leak detection test (tt) and the cycle counter (nc) are reset to zero, pursuant to step 186. Controller 54 then goes into the WAIT MODE, pursuant to step 187.

If, however, the time between the last two calls for heat (td) is greater than 120 seconds (step 178) and there is a thermostat call for heat (step 188), the furnace will remain in operation until the demand for heat has been satisfied. When the demand for heat has been satisfied and there is no longer a thermostat call for heat (step 188), the wait time clock is reset (tw=0) and restarted, pursuant to step 189, and blower 18 is started, pursuant to step 190. Blower 18 remains in operation for thirty seconds (step 192), after which time blower 18 is stopped (step 194). The wait time clock is again reset (tw=0) and restarted, pursuant to step 196. If the elapsed time since the time clock was reset and restarted, pursuant to step 176, exceeds fourteen days (step 198), the ALARM MODE is indicated (step 184) and controller 54 will execute the alarm routine, beginning at B in FIG. 7. If the elapsed time does not exceed fourteen days (step 198) and the wait time since last reset has exceeded thirty seconds (step 200), the routine branches back to step 188 to determine whether there is another thermostat call for heat, unless there is a manual reset, pursuant to step 185. As previously explained, in response to a manual reset, the time clock (t), the time of the previous call for heat (ta), the time of the last leak detection test (tt) and the cycle counter (nc) are reset to zero, pursuant to step 186, and controller 54 goes into the WAIT MODE, pursuant to step 187.

One skilled in the art will recognize that in both the FAULT 1 MODE and the FAULT 2 MODE, blower 18 is cycled on and off when the furnace is not in operation, to indicate a fault condition. Cycling blower 18 will result in intermittent blasts of cool air into the indoor space, which should alert the occupants of the presence of a fault condition. In contrast to the ALARM MODE, in which normal furnace operation is interrupted, in the FAULT 1 MODE and FAULT 2 MODE, the furnace heating cycle is not interrupted.

Referring now to FIGS. 3 and 9–11, the leak detection test routine is depicted. This routine is executed in response to any of the three test modes (TEST 1 MODE, TEST 2 MODE or TEST 3 MODE). Pursuant to step 202, a general counter (GC), fault counters (FC1, FC2) and alarm counters (A1, A2) are reset to zero, except in the case of the test routine being entered at D from the power on routine depicted in FIG. 6. If the test routine is entered from the power on routine, the test routine is entered between step 202 and step 204. Pursuant to step 204, sensor 26 is energized. Energization of sensor 26 enables sensor 26 to measure carbon dioxide concentrations in the ambient air, as will be described in greater detail hereinafter. Pursuant to step 206, a sensor/system self check is run to determine whether there is a permanent fault condition in a component of the leak detection apparatus (FAULT 1). If a permanent fault condition is indicated, pursuant to step 208, the routine goes to G in FIG. 10, which will be described hereinafter.

If, pursuant to step 208, the sensor/system check reveals no permanent fault, controller 54 determines whether the TEST 1 MODE is indicated, pursuant to step 210. If the TEST 1 MODE is indicated, controller 54 will wait until there is a thermostat call for heat, pursuant to step 212, and will wait until the demand for heat has been satisfied (step 214) to start the wait time clock (tw=0), pursuant to step 216. When the wait time clock is started, blower 18 is also started, pursuant to step 218, and controller 54 begins logging temperature data from sensor T1, which is the sensor proximate to the furnace heat exchanger and slightly downstream thereof, pursuant to step 220. By logging T1 data, controller 54 determines the cooldown rate of the heat exchanger, with blower 18 blowing supply air across the heat exchanger to expedite cooldown. Controller 54 continues to log T1 data for 180 seconds (step 222), after which time the cooldown data is used to compute the temperature of the "cool" heat exchanger (TX), pursuant to step 224. Blower 18 is then stopped pursuant to step 226.

Sensor T1 is used to infer the temperature of the heat exchanger. The temperature measured by sensor T1 is a function of the ambient air temperature in the supply air duct downstream of the heat exchanger, the ambient air flow rate and the heat exchanger temperature. For a particular furnace, a target heat exchanger temperature (which represents the temperature of a "cool" heat exchanger) has a corresponding temperature measured by sensor T1 which is a function of the ambient air temperature. Through experimental measurements, a correlation is developed between the ambient air temperature and the furnace heat exchanger cooldown temperature profile. For a predetermined target heat exchanger temperature, an additional correlation is developed between the temperature measured by sensor T1 and the ambient air temperature. In application, the cooldown temperature profile is measured. The ambient air temperature and the target temperature TX are then computed using the correlations. The correlations may be combined to provide a single correlation between the target temperature TX and the cooldown temperature profile.

Figure 10:
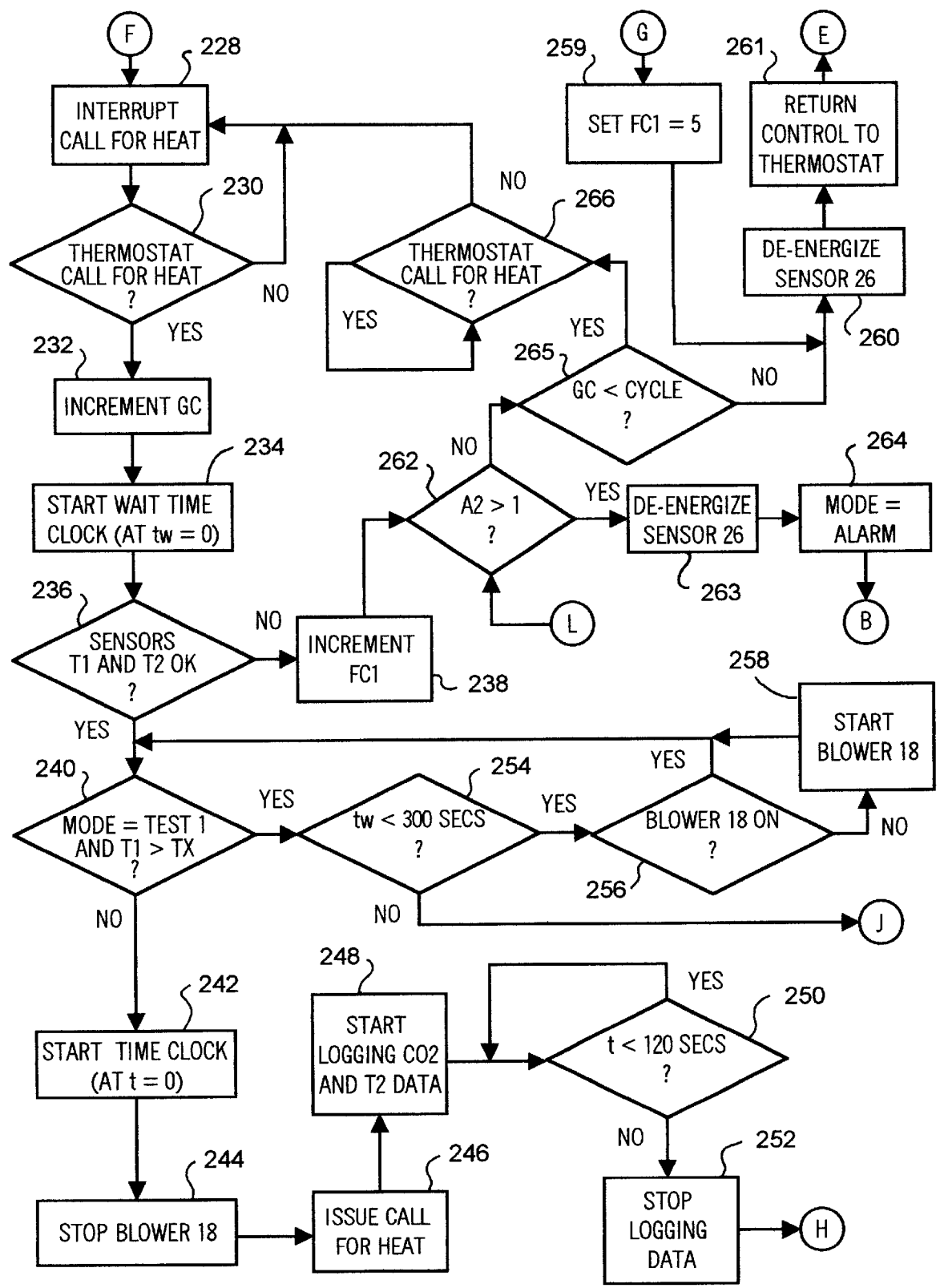

Continuing at F in FIG. 10, controller 54 opens thermostat relay 46 (FIG. 3) to interrupt a call for heat signal from thermostat 44, pursuant to step 228. When a call for heat is indicated, pursuant to step 230, the general counter (GC) is incremented, pursuant to step 232, and the wait time clock is started at zero (tw=0), pursuant to step 234. Controller 54 then checks temperature sensors T1 and T2 (step 236) and if a problem is indicated with either sensor, fault counter FC1 is incremented, pursuant to step 238. If no fault condition is indicated in either temperature sensor, controller 54 determines whether the mode is the TEST 1 MODE and whether T1 is greater than TX, pursuant to step 240. In order for the TEST 1 MODE to be executed, the temperature of the heat exchanger (T1) must not be greater than the "cool" heat exchanger temperature (TX). An excess heat exchanger temperature heats the ambient air in the vicinity of the heat exchanger, which sets up a draft in the furnace and carries carbon dioxide away from the source of the heat exchanger leak, thereby diffusing the carbon dioxide so that it is less susceptible to detection by sensor 26.

If either of the conditions of step 240 is not satisfied, the time clock is started (t=0), pursuant to step 242, blower 18 is stopped, pursuant to step 244, and the thermostat call for heat, which was interrupted pursuant to step 228, is issued, pursuant to step 246. Sensor 26 begins measuring carbon dioxide concentration in the ambient air and temperature sensor T2 begins measuring the temperature of the ambient air, pursuant to step 248. The carbon dioxide and temperature measurements continue for 120 seconds (step 250), after which time the measurements are discontinued pursuant to step 252, and the routine goes to H in FIG. 11, which will be described hereinafter.

Referring again to step 240, if both of the conditions of step 240 are satisfied, controller 54 determines whether the wait time (tw) is less than 300 seconds, pursuant to step 254. If the wait time is less than 300 seconds and blower 18 is in operation (step 256), controller 54 will again determine whether the conditions of step 240 are satisfied. In order to perform a leak detection test in the TEST 1 MODE, the heat exchanger temperature T1 must not exceed the "cool" heat exchanger temperature TX, as described hereinabove. If the leak detection test is being performed in either the TEST 2 MODE or the TEST 3 MODE, it is not necessary for the heat exchanger temperature T1 to be less than or equal to the "cool" temperature TX. If blower 18 is not in operation, it will be started, pursuant to step 258. If the wait time (tw) is greater than or equal to 300 seconds (step 254), the routine goes to J in FIG. 11, which will be described hereinafter. If the wait time is not less than 300 seconds, a fault condition is indicated because the heat exchanger has not cooled down sufficiently in the allotted time (300 seconds) to execute the leak detection test in the TEST 1 MODE.

Continuing at G in FIG. 10, in response to a permanent fault condition (step 208 in FIG. 9), fault counter FC1 is set at five (FC1=5), pursuant to step 259, carbon dioxide sensor 26 is de-energized, pursuant to step 260, and control of the furnace is returned to thermostat 44, pursuant to step 261. The routine then goes to E in FIG. 12, which will be described hereinafter.

Referring again to step 236, if there is a problem with either temperature sensor T1 or T2, fault counter FC1 is incremented, pursuant to step 238. If an alarm counter A2 exceeds one (step 262), carbon dioxide sensor 26 is de-energized, pursuant to step 263 and the ALARM MODE is indicated, pursuant to step 264. Controller 54 then executes the alarm routine, beginning at B in FIG. 7. If alarm counter A2 does not exceed one in step 262, controller 54 next determines whether general counter GC is less than the number of leak detection test cycles (CYCLE) to be run, pursuant to step 265. For example, if general counter GC is set at five, after five leak detection tests have been run, carbon dioxide sensor 26 is de-energized, pursuant to step 260 and the control of the furnace is returned to thermostat 44, pursuant to step 261. If the maximum of number of tests has not been run, controller 54 determines whether there is a thermostat call for heat, pursuant to step 266, and delays the next leak detection test until the thermostat call for heat has been satisfied. When the thermostat call for heat has been satisfied, controller 54 interrupts the next call for heat, pursuant to step 228, and then waits for the next thermostat call for heat (step 230) to begin the next leak detection test cycle.

Figure 11:
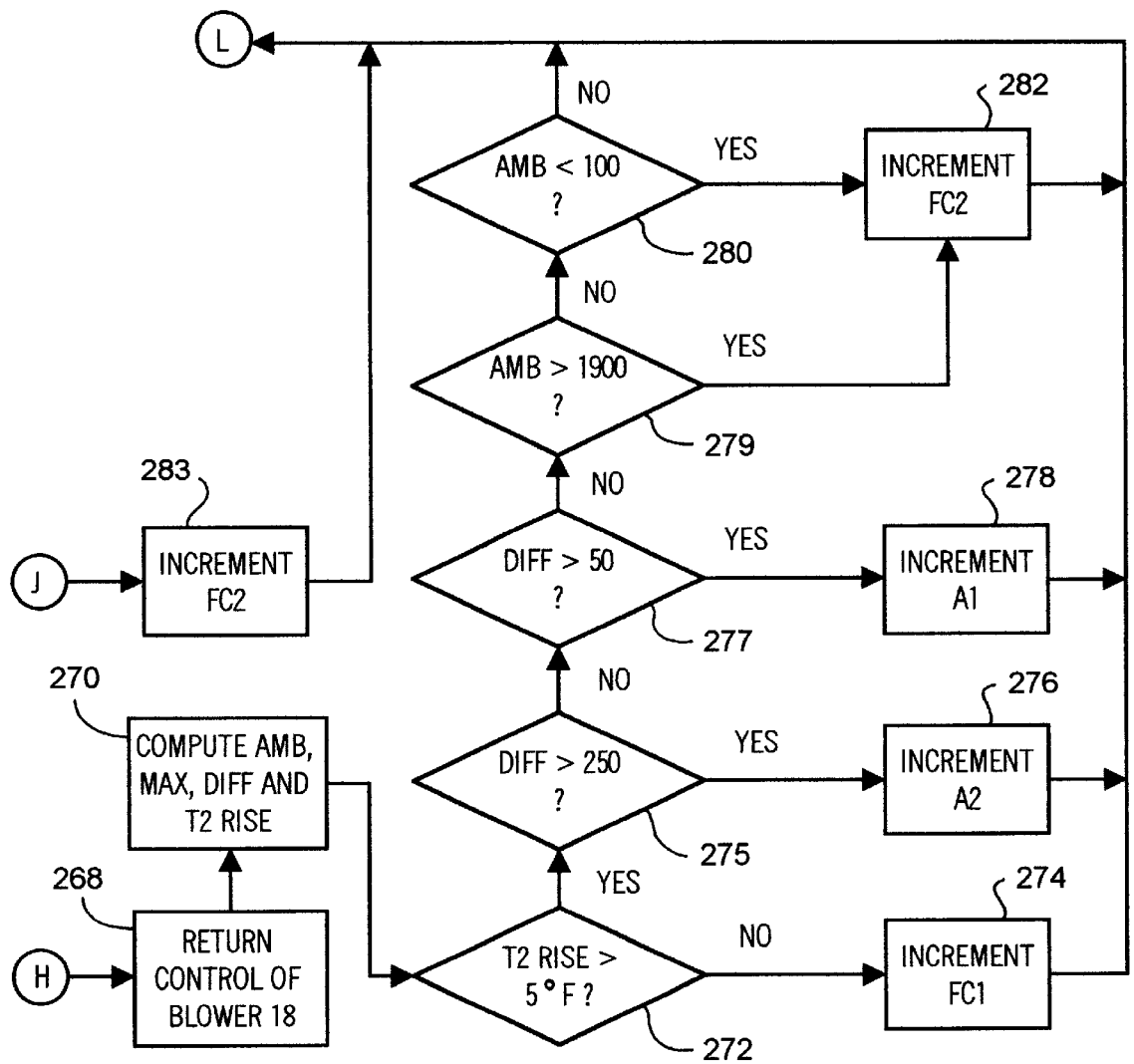

Continuing now at H in FIG. 11, after the carbon dioxide and temperature data have been logged, pursuant to steps 248 through 252 during the 120 second sampling period after the call for heat is issued, pursuant to step 246, the control of blower 18 is returned to thermostat 44 and furnace controller 48, pursuant to step 268. The ambient (AMB), maximum (MAX) and differential (DIFF) carbon dioxide concentrations are computed in response to the data measured by sensor 26 and the rise in ambient air temperature is computed in response to the data measured by temperature sensor T2, pursuant to step 270. The ambient carbon dioxide concentration corresponds to the level of carbon dioxide in the ambient air downstream of the furnace heat exchanger during the first thirty seconds of the 120 second sampling period. The maximum carbon dioxide concentration corresponds to the maximum level of carbon dioxide in the ambient air downstream of the heat exchanger, as measured during the 120 second sampling period. The differential is the maximum concentration minus the ambient concentration.

Typically, during the first thirty seconds of the sampling period, furnace combustion has not yet started so that no carbon dioxide is being produced by the furnace. However, after the first thirty seconds, the furnace is in operation and is producing carbon dioxide. Therefore, if there is a leak in the furnace heat exchanger, one would expect the level of carbon dioxide in the ambient air to increase during the 120 second sampling period. Therefore, if a substantial increase in carbon dioxide concentration is measured by sensor 26 during the sampling period, it is indicative of a potential leak in the heat exchanger. Similarly, as the furnace warms up, one would expect an increase in the temperature of the ambient air in sampling tube 28. Therefore, temperature sensor T2 should measure an increase in ambient air temperature during the 120 second measurement period. If the increase is not greater than a predetermined amount (e.g., 5° F.), pursuant to step 272, first fault counter FC1 is incremented, pursuant to step 274, which indicates a problem with the leak detection apparatus, in this case, either a problem with temperature sensor T2 or an insufficient flow of ambient air to gas sensor 26.

If temperature sensor T2 indicates a temperature increase of more than 5° F., as expected, controller 54 assumes that the leak detection test and the data measured are valid. Controller 54 then determines whether the carbon dioxide differential is greater than 250 parts per million (ppm), pursuant to step 275. If the differential is greater than 250 ppm, alarm counter A2 is incremented, pursuant to step 276. If the carbon dioxide differential is not greater than 250 ppm (step 275), controller 54 next determines whether the differential is greater than 50 ppm, pursuant to step 277. If it is, a second alarm counter A1 is incremented, pursuant to step 278. If the carbon dioxide differential is not greater than 50 ppm, then neither alarm counter A2 or A1 is incremented.

Controller 54 next determines whether the ambient carbon dioxide concentration is greater than 1900 ppm or less than 100 ppm, pursuant to steps 279 and 280. If either condition occurs, it indicates an abnormally high or low ambient carbon dioxide level, which results in second fault counter FC2 being incremented, pursuant to step 282. If the ambient carbon dioxide concentration is between 100 and 1900 ppm, fault counter FC2 is not incremented and the routine goes to L in FIG. 10.

Continuing at L in FIG. 10, if alarm counter A2 exceeds one (step 262), which will occur if two leak detection tests in a cycle yield a carbon dioxide differential greater than 250 ppm (step 275), sensor 26 is de-energized (step 263) and the ALARM MODE is indicated (step 264). The alarm routine is then executed, beginning at B in FIG. 7. Continuing at J in FIG. 11, if the wait time (tw) is greater than or equal to 300 seconds (step 254), fault counter FC2 is incremented, pursuant to step 283 and the routine goes to L in FIG. 10.

Figure 12:
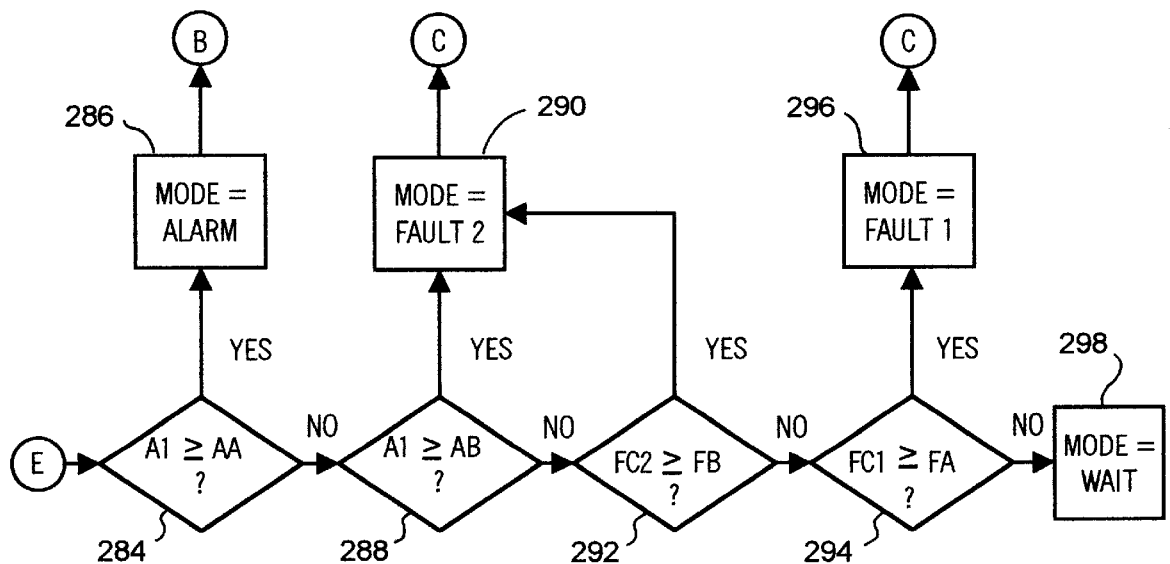

Referring also to FIG. 12, after the prescribed number of leak detection tests (CYCLE) has been performed and control of the furnace has been returned to thermostat 44, pursuant to step 261, controller 54 executes the routine depicted in FIG. 12, beginning at E. If alarm counter A1 equals or exceeds predetermined count AA (step 284), the ALARM MODE is triggered, pursuant to step 286. In response to the ALARM MODE, controller 54 executes the alarm routine, beginning at B in FIG. 7. However, if alarm counter A1 does not equal or exceed AA, but does equal or exceed a second predetermined value AB, pursuant to step 288, the FAULT 2 MODE is triggered, pursuant to step 290, and the fault routine is executed, beginning at C in FIG. 8. If alarm counter A1 does not equal or exceed AB, controller 54 next determines whether fault counter FC2 equals or exceeds a predetermined value FB, pursuant to step 292. If so, the FAULT 2 MODE is triggered, pursuant to step 290. If the second fault counter FC2 is not greater than or equal to FB, controller 54 determines whether fault counter FC1 equals or exceeds a predetermined value FA, pursuant to step 294. If so, the FAULT 1 MODE is triggered, pursuant to step 296, and the fault routine is executed, beginning at C in FIG. 8. If not, controller 54 goes into the WAIT MODE, pursuant to step 298.

As indicated in FIG. 10, the prescribed number of leak detection tests (CYCLE) indicated by general counter GC will be performed, unless the tests are aborted by alarm counter A2 exceeding one. The routine depicted in FIG. 12 is performed only after all of the prescribed number of leak detection tests have been performed. The following Table 1 illustrates the different modes of operation of controller 54.

TABLE 1

System Operating Modes and Indications

| MODE | Description | set CYCLE | set AA | set AB | set FA | set FB | Visual Indication Green-1 | Green-2 |
|---|---|---|---|---|---|---|---|---|
| WAIT | System Normal, Waiting | * | * | * | * | * | flashing | flashing[1] |
| TEST1 | Normal Test | 5 | 3 | 2 | 3 | 3 | flashing | steady on |
| TEST2 | Warm HX Test | 3 | 2 | 1 | 2 | 2 | steady on | flashing |
| TEST3 | Manual Test | 1 | 1 | 1 | 1 | 1 | off | flashing |
| ALARM | Alarm | * | * | * | * | * | flashing | flashing[2] |

TABLE 1-continued

System Operating Modes and Indications

| MODE | Description | set CYCLE | set AA | set AB | set FA | set FB | Visual Indication Green-1 | Green-2 |
|---|---|---|---|---|---|---|---|---|
| FAULT1 | System Fault | * | * | * | * | * | steady on | steady on |
| FAULT2 | External Fault | * | * | * | * | * | flashing | off |

[1]flash together with Green-1
[2]flash alternately with Green-1

For example, Table 1 indicates that in the TEST 1 MODE, the number of leak detection tests to be performed (CYCLE) is set at five. The predetermined values of alarm counter A1 (AA and AB) are set at three and two, respectively, and the predetermined values of fault counter FC1 and fault counter FC2 (FA and FB) are set at three. In the TEST 2 MODE, in which the furnace heat exchanger (HX) does not have to cool down to temperature TX or below, the number of tests (CYCLE) are set at three and the alarm counts (AA and AB) are set at two and one, respectively. FA and FB, which trigger the FAULT 1 MODE and the FAULT 2 MODE, respectively, are set at two. In the TEST 3 MODE, which is triggered in response to a manual call for test, only one leak detection test is performed (CYCLE=1) and the other values (AA, AB, FA and FB) are also set at one. Therefore, the ALARM MODE and the FAULT 1 and FAULT 2 MODES may be triggered under different circumstances, depending on what test mode is being performed.

Indicator lights 58 are also controlled by controller 54, as previously explained with reference to FIG. 3. Indicator lights 58 are used to indicate the particular mode in which controller 54 is operating, as shown in the last two columns of Table 1.

Figure 13:
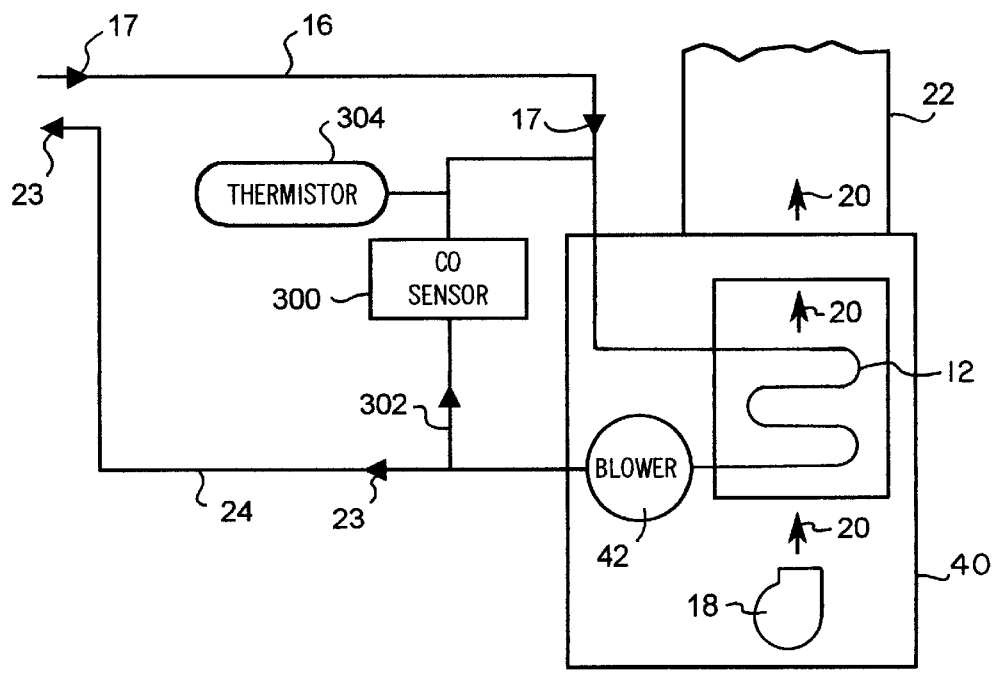
FIG. 13 is a schematic diagram of apparatus for detecting carbon monoxide in products of combustion from a furnace.

Referring now to FIG. 13, apparatus for measuring a particular gas, such as carbon monoxide, in the products of combustion of furnace 40 is shown. Furnace 40 includes a heat exchanger 12 in which products of combustion are circulated for heating air blown across heat exchanger 12 by blower 18, as described hereinabove with reference to FIG. 2. An induced draft blower 42 draws products of combustion through heat exchanger 12 and outwardly from furnace 40 through flue 24. The apparatus includes a gas sensor 300 and a sampling tube 302, which is in fluid communication between flue 24 and air intake conduit 16. Sensor 300 is preferably a carbon monoxide sensor of the metal oxide type, manufactured and sold by Yazaki Meter Co., of Tokyo, Japan, under model number YS-710.

A temperature sensor 304, preferably a thermistor, is located to measure the temperature of the flue gas within tube 302. The pressure difference between conduit 16 and flue 24 provided by blower 42 when furnace 40 is in operation draws a sample of the products of combustion from flue 24 into tube 302. The sample of products of combustion flows through tube 302 and is drawn back into furnace 40 through conduit 16. No pump or other mechanical device is needed to transport the sample to sensor 300. Sensor 300 measures the carbon monoxide concentration in the products of combustion sample in tube 302 during a predetermined sampling period (e.g., 120 seconds) beginning just prior to the onset of furnace combustion and continuing after the onset of combustion. Temperature sensor 304 should detect an increase in temperature of the products of combustion in tube 302 during the sampling period. This increase in temperature is an indication of sufficient flow of products of combustion within tube 302 for sampling purposes.

In accordance with the present invention, improved apparatus for sampling gas in operative association with a combustion appliance is provided. One application of the present invention is in detecting products of combustion leakage in a combustion appliance, such as a furnace, using a selected gas known to be present in the products of combustion, such as carbon dioxide. The leak detection apparatus according to the present invention can be used to automatically detect products of combustion leakage in a combustion appliance without the need to introduce a tracer gas or the like or other special procedures, which typically require a service technician. Another application of the gas sampling apparatus, according to the present invention, is to detect a selected gas, such as carbon monoxide, in products of combustion.

Various embodiments of the invention, including the best mode, have now been described in detail. Since changes in and/or additions to the above-described embodiments may be made without departing from the nature, spirit or scope of the invention, the invention is not to be limited to the above-described details, but only by the appended claims and their equivalents.

What is claimed is:

1. In a combustion appliance having a first conduit through which combustion air is provided to the appliance and a second conduit through which a gas is discharged from the appliance after being heated, apparatus for sampling the heated gas to determine whether a selected gas is present in the heated gas, said apparatus comprising:

a third conduit communicating between the first and second conduits; and a gas sensor operable to sense the selected gas in said third conduit, a sample of the heated gas being drawn from the second conduit into said third conduit by a pressure difference between the first and second conduits when the appliance is in operation, the heated gas being ambient air external to products of combustion carrying components of the appliance.

2. Apparatus of claim 1 further including a flow sensor operable to determine whether there is sufficient flow of the sample of heated gas in said third conduit for sampling purposes.

3. Apparatus of claim 2 wherein said flow sensor includes a temperature sensor for sensing temperature of the sample of heated gas in said third conduit.

4. Apparatus of claim 3 further including a heater operably associated with said third conduit to further heat the sample of heated gas in said third conduit before the sample is sensed by said temperature sensor.

5. Apparatus of claim 1 wherein the selected gas is carbon dioxide.

6. A combustion appliance, comprising:

a first conduit through which combustion air is provided to said appliance;

a second conduit through which a gas is discharged from said appliance after being heated; and apparatus for sampling the heated gas to determine whether a selected gas is present in the heated gas, said apparatus including a third conduit communicating between said first and second conduits, a gas sensor operable to sense the selected gas in said third conduit, a sample of the heated gas being drawn from said second conduit into said third conduit by a pressure difference between said first and second conduits when said appliance is in operation, the heated gas being ambient air external to products of combustion carrying components of said appliance.

7. Appliance of claim 6 further including a flow sensor operable to determine whether there is sufficient flow of the sample of heated gas in said third conduit for sampling purposes.

8. Appliance of claim 7 wherein said flow sensor includes a temperature sensor for sensing temperature of the sample of heated gas in said third conduit.

9. Appliance of claim 8 further including a heater operably associated with said third conduit to further heat the sample of heated gas in said third conduit before the sample is sensed by said temperature sensor.

10. Appliance of claim 6 wherein the selected gas is carbon dioxide.

* * * * *